United States Patent
Giselbrecht

(10) Patent No.: US 10,683,245 B2
(45) Date of Patent: Jun. 16, 2020

(54) PROCESS FOR MANUFACTURING 1-CYCLOPROPYL-NAPHTHALENES

(71) Applicant: PATHEON AUSTRIA GMBH & Co KG, Linz (AT)

(72) Inventor: Karl-Heinz Giselbrecht, Linz (AT)

(73) Assignee: Patheon Austria GMBH & Co. KG, Linz (AT)

( * ) Notice: Subject to any disclaimer, the term of this patent is extended or adjusted under 35 U.S.C. 154(b) by 0 days.

(21) Appl. No.: 15/736,420

(22) PCT Filed: Jun. 29, 2016

(86) PCT No.: PCT/EP2016/065201
§ 371 (c)(1),
(2) Date: Dec. 14, 2017

(87) PCT Pub. No.: WO2017/001516
PCT Pub. Date: Jan. 5, 2017

(65) Prior Publication Data
US 2018/0186706 A1 Jul. 5, 2018

(30) Foreign Application Priority Data

Jun. 29, 2015 (EP) ................. 15174227

(51) Int. Cl.
*C07C 1/32* (2006.01)
*C07D 231/06* (2006.01)

(52) U.S. Cl.
CPC .......... *C07C 1/323* (2013.01); *C07D 231/06* (2013.01); *C07C 2601/02* (2017.05)

(58) Field of Classification Search
CPC .... C07C 1/32; C07C 7/00; C07C 7/08; C07C 7/11
See application file for complete search history.

(56) References Cited

FOREIGN PATENT DOCUMENTS

| CN | 102391059 A | 3/2012 |
|---|---|---|
| CN | 103664471 A | 3/2014 |
| WO | 2006026356 A2 | 3/2006 |
| WO | 2009070740 A2 | 6/2009 |
| WO | 2011085009 A2 | 7/2011 |
| WO | 2011126852 A2 | 10/2011 |
| WO | 2011159732 A1 | 12/2011 |
| WO | 2010028189 A2 | 3/2012 |
| WO | 2012092395 A2 | 7/2012 |
| WO | 2014008295 A1 | 1/2014 |

OTHER PUBLICATIONS

Wang et al. (Radical ion probes. Part 10. Ceric (IV) ammonium nitrate oxidation of cyclopropylarenes, J. Chem. Soc., Perkin Trans. 2, 1998, 2705-2711) (Year: 1998).*
Shabarov et al. (Cyclopropanes and cyclobutanes. XXX. Cyclopropanes and cyclobutanes with p-diphenyl and naphthyl radicals, Journal of General Chemistry USSR, vol. 33, No. 7, p. 2199-2123) (Year: 1963).*
Database CA (Chemical Abstracts Service, Database accession No. 1956:60253) (Year: 1963).*
Wiley (Chemistry of Heterocyclic Compounds, vol. 22, Chapter 8. Chemistry of the pyazolines, 1967 John Wiley and Sons, Ltd.) (Year: 1967).*
Partial European Search Report for European Patent Application No. 15174227.7, dated Dec. 16, 2015, 6 pages.
Extended European Search Report for European Patent Application No. 15174227.7, dated Apr. 29, 2016, 13 pages.
International Search Report and Written Opinion for International Patent Application No. PCT/EP2016/065201, dated Oct. 4, 2016, 20 pages.
Kost et al., "Reactions of Hydrazine Derivatives. III. 3-Arylpyrazolines," XP-002752262. Chemical Abstracts retrieved from STN Database accession No. 1956:60253.
Shabarov et al., "Cyclopropanes and Cyclobutanes. XXX. Cyclopropanes and Cyclobutanes with p-Diphenyl and Naphthyl Radicals," (Moscow M. V. Lomonosov State University, translated from Zhurnal Obshchei Khimii, vol. 33:7 pp. 2119-2123 (1963) XP008178273.
Lemhadri et al., "Suzuki Coupling of Cyclopropylboronic Acid With Aryl Halides Catalyzed by a Palladium-Tetraphosphine Complex", Synthetic Communications, 36: 121-128, 2006 (8 pages).
Molander et al., "Cross-Coupling of Mesylated Phenol Derivatives with Potassium Cyclopropyltrifluoroborate", J. Org. Chem. 2011, 76, 8126-8130 (5 pages).
Zhang et al., "Facile synthesis of aryl(het)cyclopropane catalyzed by palladacycle", Tetrahedron 68 (2012), 900-905 (6 pages).

(Continued)

*Primary Examiner* — Youngsul Jeong
(74) *Attorney, Agent, or Firm* — Raymond G. Arner; Pierce Atwood LLP

(57) ABSTRACT

A process for preparing 1-cyclopropyl-naphthalene derivatives of Formula (1) wherein $R_1$-$R_7$ are independently hydrogen, alkyl, alkoxy, cycloalkyl or aryl comprising the steps of a) contacting an acid salt of a 1-naphthyl-2-aminoethylketone with a base and a first solvent to obtain a solution wherein the molar ratio of base to 1-naphthyl-2-aminoethylketone acid salt is at least 0.7, b) addition of hydrazine to obtain a 3-(1-naphthyl)-1H-pyrazoline, c) optionally adding a second solvent and/or at least partially removing the first solvent, and d) heating the reaction mixture to a temperature above 190° C. to obtain the compound of Formula (1).

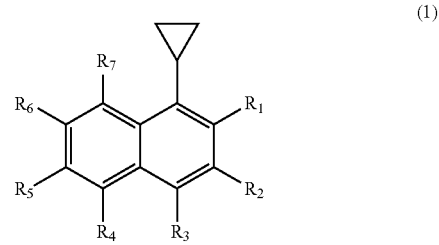

(1)

9 Claims, No Drawings

(56) References Cited

OTHER PUBLICATIONS

Nishiyama et al., "Lanthanum metal-assisted cyclopropanation of alkenes with gem-dihaloalkanes", Tetrahedron Letters 48 (2007) 6405-6407 (3 pages).
Kost et al., "Reactions of hydrazine derivatives. III. 3-Arylpyrazolines", Vestnik Moskovskogo Universiteta (1955) 10 (No. 12).
Europe, European Office Action dated Sep. 3, 2019 for European Application No. 15174227.7.
C.H. Jarboe: "Chemistry of the Pyrazolines", In: "Chemistry of Heterocyclic Compounds, vol. 22", John Wiley & Sons, Ltd., XP055616326, pp. 209-278.

* cited by examiner

PROCESS FOR MANUFACTURING 1-CYCLOPROPYL-NAPHTHALENES

CROSS REFERENCE TO RELATED APPLICATIONS

This application is a U.S. National Stage of PCT International Application No. PCT/EP2016/065201, filed Jun. 29, 2016, which claims priority to European Patent Application No. 15174227.7, filed Jun. 29, 2015, the entire contents of which is incorporated herein by reference.

The present invention relates to a process for the production of 3-(1-napthalenyl)-1H-pyroazole derivatives and further pertains to the production of 1-cyclopropyl-naphthalene derivatives.

BACKGROUND OF THE INVENTION 1-cyclopropyl-naphthalene derivatives are important intermediates for organic synthesis. For example 1-cyclopropyl naphthalene is used in the manufacture of fungicides, and of pharmaceutically active compounds to treat for example disorders of uric acid metabolism (see e.g. WO 2010/028189) or HIV infections (see e.g. WO 2006/026356). Specific examples of such pharmaceutically active compounds could be 2-(5-bromo-4-(4-cyclopropylnaphthalen-1-yl)-4H-1,2,4-triazol-3-ylthio)acetate or any metabolite, pharmaceutically acceptable salt, solvate, ester, tautomer or prodrug thereof as disclosed in e.g. WO 2009/070740 A2, WO 2011/126852 A2 and WO 2011/159732 A1.

Known synthetic methods for the preparation of cyclopropyl-naphthalene are performed by a palladium-catalyzed Suzuki reaction of an aryl halide with cyclopropyl boronic acid as is disclosed by Lemhadri et. al. in Synthetic Communications (2006) 36(1) 121-128, CN 102391059, and by Zhang et. al. in Tetrahedron (2012), 68(3), 900-905, Suzuki reactions of a heteroaryl mesylate with cyclopropyl trifluoroborate are further disclosed by Molander et. al. in J. Org. Chem. 2011, 76, 8126-8130. A disadvantage of such Suzuki reactions is, the use of expensive starting materials and catalysts which makes such reactions less attractive from a commercial point of view.

Alternatively, reactions of gem-dihalo alkanes with alkenes in the presence of lanthanum metal catalysts are disclosed by Nishiyama et. al. in Tetrahedron Letters (2007), 48(36), 6405-6407. The applied rare earth metal lanthanum is very expensive and is therefore not suitable for use in industrial production.

Processes using Grignard reagents are also known. CN 103664471, discloses reactions of 1-vinylnapthalene with gem-dihalo alkanes with alkyl-MgCl. Kumada coupling reactions of 1-bromonaphthalene with suitable Grignard reagents are disclosed in WO 2014/008295, WO 2012/092395, WO 2011/085009, WO 2010/028189. On the one hand Grignard reagents are expensive and generally not easy to prepare. More importantly Grignard reactions are exothermic in nature and pose safety risks and demand a more complex process control.

The preparation of cyclopropyl-naphthalene by catalytic decomposition of the corresponding pyrazolones synthesized from hydrochlorides of Mannich bases is disclosed by Shabarov et al. in Zhurnal Obshchei Khimii (1963), 33(7), 2119-2123. The disadvantage of this process is that the product is obtained in a low yield and significant formation of undesirable side products generally arise.

The object of the present invention is to overcome the above disadvantages and to provide an improved process.

SUMMARY OF THE INVENTION

The object of the invention is achieved by a process for preparing a compound of Formula (1)

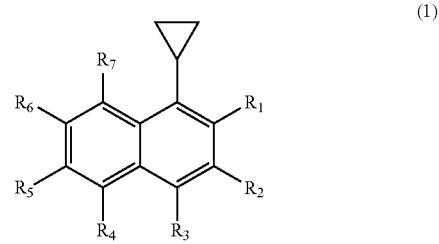

wherein $R_1$-$R_7$ are independently hydrogen, alkyl, alkoxy, cycloalkyl or aryl comprising the steps of
a) contacting a compound of Formula (2)

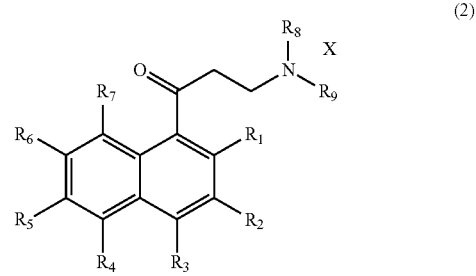

wherein $R_1$-$R_7$ are the same as above and $R_8$ and $R_9$ are independently hydrogen, $C_1$-$C_8$ alkyl and X is a counter acid, with a base and a first solvent to obtain a solution wherein the molar ratio of base to compound of Formula (2) is at least 0.7;
b) addition of hydrazine to obtain a compound of Formula (3)

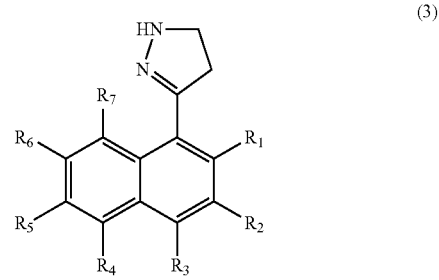

wherein $R_1$-$R_7$ are the same as above;
c) optionally adding a second solvent and/or at least partially removing the first solvent; and
d) heating the reaction mixture to a temperature above 190° C. to obtain the compound of Formula (1).

The process of the present invention allows for the production of Formula (1) with a high yield. Typically yields above 50% are obtained and even yields exceeding 90% have been achieved. In contrast, Shabarov et al. (1963)

obtained a yield of 20% when starting from a compound of Formula (2) as the present invention does. Furthermore the current process allows for a lower amount of side products (e.g. 1-methyl napthalene) to be formed. In addition the process of the present invention has generally lower safety risks than alternative processes using Grignard reagents and can readily be scaled up for industrial production and enable a less complex process control. The process of the invention is generally more cost efficient than the alternative processes using relatively expensive catalysts and starting materials. In addition with the process of the invention the compound of Formula (1) can be obtained at a high purity level. The high purity level can be reached because of the easy separation of undesired contaminants.

The invention provides a process for preparing 1-cyclopropyl-naphtalene derivatives of Formula (1) having substituents $R_1$-$R_7$ as defined above. Preferably $R_1$-$R_7$ are independently hydrogen, $C_1$-$C_8$ alkyl, $C_1$-$C_6$ alkoxy, $C_3$-$C_{10}$ cycloalkyl or $C_5$-$C_{10}$ aryl. More preferably $R_1$-$R_7$ are independently selected from the group consisting of hydrogen, methyl, ethyl, n-propyl, iso-propyl, n-butyl, iso-butyl, tert-butyl, methoxy, ethoxy, propoxy, cyclopropyl, cyclobutyl, cycloheptyl, phenyl, benzyl, naphthyl, and tolyl. Most preferably $R_1$-$R_7$ are hydrogen.

With the term "independently" is meant that each of the substituents $R_1$-$R_7$ may be chosen individually. Each of $R_1$-$R_7$ can be different or the same; this means that also one of $R_1$-$R_7$ can be different from the others. For example $R_2$ is methyl and $R_1$ and $R_3$-$R_7$ are all hydrogen. The substituents of $R_1$-$R_7$ may be branched and/or substituted.

A starting material used in step a) of the process of the invention is the compound of Formula (2). The substituents of $R_1$-$R_7$ in said compound are the same as defined above for the compound of Formula (1). Preferably $R_8$ and $R_9$ are independently selected from the group consisting of hydrogen, methyl, ethyl, n-propyl, iso-propyl, n-butyl, iso-butyl and tert-butyl. More preferably $R_8$ and $R_9$ are independently methyl or ethyl. Most preferably $R_8$ and $R_9$ are methyl. X is generally selected as known in the art. Examples for the selection of X are provided by P. H. Stahl and C. G. Wermuth, editors, *Handbook of Pharmaceutical Salts: Properties, Selection and Use*, Weinheim/Zürich:Wiley-VCH/VHCA, 2002. Thus, suitable examples include hydrochloric acid, hydrobromic acid, sulfuric acid, phosphoric acid and oxalic acid.

Compound of Formula (2) in step a) is used in an amount of at least 0.1 weight percent (wt %) and at most 70 wt %, based on the total weight of solvent and compound of Formula (2). Preferably the amount is at least 1 wt %, more preferably at least 2 wt %, and most preferably at least 5 wt %, and preferably at most 60 wt %, more preferably at most 50 wt %, and most preferably at most 40 wt %, based on the total weight of solvent and compound of Formula (2).

Compound of Formula (2) may be prepared by any feasible synthesis method known to the skilled artisan. For example 1-acetylnaphthalene can be subjected to aminomethylation in the conditions of the Mannich reaction to afford the corresponding ketonic Mannich base as hydrochloride.

Preferably the base used in step a) is a carbonate, an amine, a phosphate, ammonia, a metal oxide, an alcoholate or a hydroxide. More preferably the base used in step a) is a carbonate, a phosphate, ammonia, a metaloxide, an alcoholate or a hydroxide. Even more preferably the base is selected from the group consisting of $K_2CO_3$, $KHCO_3$, $Na_2CO_3$, $NaHCO_3$, $CH_3NH_2$, $(CH_3)_2NH$, $(CH_3)_3N$, pyridine, quinoline, $NH_3$, CaO, potassium tert-butoxide, aluminium isopropoxide, $Na_3PO_4$, $Na_2HPO_4$, LiOH, NaOH, KOH, $Ca(OH)_2$ and $Mg(OH)_2$. Most preferably the base is NaOH.

Preferably, the molar ratio of base to compound of Formula (2) is at least 0.7, more preferably at least 0.8, even more preferably at least 0.9, and most preferably at least 0.95, and preferably at most 1.3, more preferably at most 1.2, even more preferably at most 1.1 and most preferably at most 1.05.

The pH value of the solution of step a) including the base, the first solvent and the compound of Formula (2) is generally at least 5 and at most 14. Preferably, the pH value of the mixture including the base, the first solvent and the compound of Formula (2) in step a) is at least 6, more preferably at least 8, even more preferably at least 9 and most preferably at least 9.5; and preferably at most 13, more preferably at most 12.5, even more preferably at most 12, and most preferably at most 11.

The term "solution", as used herein, refers to a mixture of one or more solvents with one or more substances at least partially dissolved therein. In general a "solution" is a homogeneous mixture composed of only one phase.

The first solvent of step a) may be any solvent suitable for use in the process of the invention. Typically, the first solvent is capable of dissolving the compound of Formula (2). In general the first solvent under step a) is a polar solvent. Preferably, the first solvent is selected from the group consisting of water, alcohols, carbonates, organosulfur compounds and amides. More preferably, the first solvent is selected from the group consisting of water, methanol, ethanol, triethylene glycol, propylene carbonate, sulfolane, dimethylformamide and dimethylacetamide. Even more preferably, the first solvent is selected from the group consisting of water, methanol, ethanol, triethylene glycol, sulfolane, dimethylformamide and dimethylacetamide. Most preferably, the first solvent of step a) is triethylene glycol. The first solvent may also be a mixture of two or more solvents.

In an embodiment, the first solvent comprises at least one solvent with a boiling point exceeding the reaction temperature of step d). More specifically, the boiling point of the first solvent is at least 10° C. above the reaction temperature of step d), preferably at least 20° C. above the reaction temperature of step d). If the first solvent consists of two or more solvents, at least one solvent has a boiling point above the reaction temperature of step d) and at least one solvent having a boiling point below the reaction temperature of step d). In steps a) and b) one of the solvents may be water. Water may be present for example by adding water together with the base and/or water may be formed during step b). Preferably, water is removed before reaction step c). Such removal can be performed using any method known in the art. Examples of such methods include distillation and extraction.

In one embodiment of the invention, the first solvent may be capable of dissolving compounds of Formulae 1, 2 and/or 3. Preferably, the first solvent is capable of dissolving compounds of Formulae 1, 2 and 3. More preferably, the first solvent of step a) is capable of forming an azeotrope with the compound of Formula (1) which allows a more efficient isolation of the compound of Formula (1) from the reaction mixture in step d). This efficient isolation renders a process with less purification steps and a shorter processing time. An example of such a first solvent includes triethylene glycol.

With the term "azeotrope" a mixture of two or more liquids is meant whose proportions cannot be altered by simple distillation.

In general the reaction mixture in step a) is kept at ambient temperature. Preferably the temperature of the reaction mixture in step a) is at least 10° C. and at most 35° C. More preferably the temperature of the reaction mixture in step a) is at least 15° C. and most preferably the reaction mixture in step a) is at least 20° C., and more preferably at most 30° C. and most preferably at most 25° C.

The contacting of the base, first solvent and compound of Formula (2) can be in any suitable sequence. Preferably, the compound of Formula (2) is first dissolved in the first solvent, and subsequently the base is added. The base can be added in one go, in two or more portions, or continuously.

To the resulting reaction mixture of step a) subsequently hydrazine is added. The hydrazine used in step b) can be in any form known in the art. Typically the hydrazine can be anhydrous hydrazine or hydrazine monohydrate. Preferably, the hydrazine is hydrazine monohydrate. In step b) the molar ratio of hydrazine to the compound of Formula (2) is preferably at least 0.7, more preferably at least 0.8, even more preferably at least 0.85, even more preferably at least 0.9 and most preferably at least 0.95, and at most 1.3, more preferably at most 1.2, even more preferably at most 1.15, and most preferably at most 1.1.

The temperature of the reaction mixture after addition of hydrazine is preferably at least 30° C., more preferably at least 50° C., even more preferably at least 70° C. and most preferably at least 75° C., and preferably at most 170° C., more preferably at most 150° C., even more preferably at most 120° C. and most preferably at most 90° C.

After addition of the hydrazine the reaction mixture is kept at the elevated temperature for a time that is sufficient to convert compound of Formula (2) to compound of Formula (3). The mixture is generally kept at the elevated temperature for at least 1 hour and at most for 8 hours. Preferably, after addition of hydrazine the reaction mixture is kept at the elevated temperature for at least 2 hours, more preferably for at least 3 hours, even more preferably for at least 4 hours and most preferably for at least 5 hours, and preferably for at most 7 hours, even more preferably for at most 6 hours and most preferably for at most 5 hours.

Compound of Formula (3) as obtained from step b) of the described process has substituents $R_1$-$R_7$ as defined above. Preferably $R_1$-$R_7$ are independently hydrogen, $C_1$-$C_8$ alkyl, $C_1$-$C_6$ alkoxy, $C_3$-$C_{10}$ cycloalkyl or $C_5$-$C_{10}$ aryl. More preferably $R_1$-$R_7$ are independently selected from the group consisting of hydrogen, methyl, ethyl, n-propyl, iso-propyl, n-butyl, iso-butyl, tert-butyl, methoxy, ethoxy, propoxy, cyclopropyl, cyclobutyl, cycloheptyl, phenyl, benzyl, naphthyl, and tolyl. Most preferably $R_1$-$R_7$ are hydrogen.

Optionally a second solvent may be added and/or the first solvent removed from the reaction mixture in step c). Step c) may be performed concurrent to step b). Methods for removal of the first solvent are known to the person skilled in the art. Such methods for example include distillation, fractional distillation or extraction. It is also contemplated that the first solvent comprises two or more solvents, and at least one of these solvents is removed in step c).

The second solvent of step d) may be any solvent suitable for use in the process of the invention. Typically, the second solvent is capable of dissolving the compound of Formula (1). In general the second solvent under step d) is a polar solvent. Preferably, the second solvent is selected from the group consisting of alcohols, carbonates, and organosulfur compounds. More preferably, the second solvent is selected from the group consisting of triethylene glycol, propylene carbonate and sulfolane. Even more preferably, the second solvent is selected from the group consisting of triethylene glycol and sulfolane. Most preferably, the second solvent of step d) is triethylene glycol. The second solvent may also be a mixture of two or more solvents.

In an embodiment, the second solvent has a boiling point exceeding the reaction temperature of step d). More specifically, the boiling point of the second solvent is at least 10° C. above the reaction temperature of step d), preferably at least 20° C. above the reaction temperature of step d).

To obtain the compound of Formula (1) the reaction mixture which contains the compound of Formula (3) is heated to a temperature of at least 190° C., more preferably at least 210° C. and most preferably at least 220° C., and at most 300° C., more preferably at most 290° C., even more preferably at most 280° C., even more preferably at most 270° C. and most preferably at most 260° C. in step d).

A catalyst may be present in step d). In general such catalyst is a heterogeneous catalyst. Preferably such catalyst is selected from the group consisting of transition metals. More preferably such catalyst is selected from the group of Fe, Co, Ni, Ru, Rh, Pd, Os, Ir, and Pt. Most preferably such catalyst is Pt. In a preferred embodiment a catalyst is absent.

The obtained compound of Formula (1) may be isolated and purified by standard methods known by the person skilled in the art. Such methods for example include distillation, fractional distillation and extraction.

The process of the invention further may comprise the step of converting the compound of Formula (1) to a pharmaceutically active compound. Such pharmaceutically active compounds are compounds to treat for example disorders of uric acid metabolism or HIV infections. Preferred compounds are Lesinurad (CAS number: 878672-00-5) and it salts, for example Lesinurad sodium (CAS number: 1151516-14-1). Most preferred is Lesinurad.

The invention further pertains to a process for preparing a compound of Formula (3)

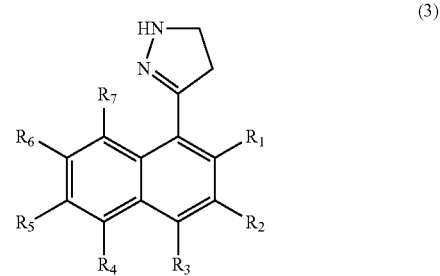

wherein $R_1$-$R_7$ are the same as defined above for the compound of Formula (1), comprising the steps of
a) contacting a compound of Formula (2)

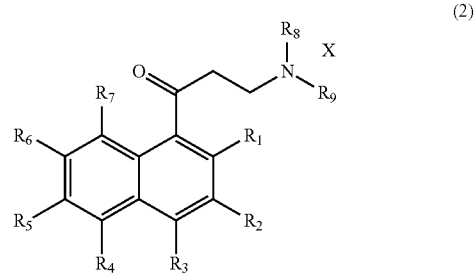

wherein $R_1$-$R_7$, $R_8$, $R_9$ and X are the same as above for the compound of Formula (2), with a base and a solvent to obtain a solution wherein the molar ratio of base to compound of Formula (2) is at least 0.3; and
b) addition of hydrazine to obtain the compound of Formula (3).

Specific details for steps a) and b) of this process have been described above and apply accordingly.

The disclosed process and parameters lead to a high yield of the compound of Formula (1); i.e. a yield of more than 90% can be obtained. In addition, the compound of Formula (1) is obtained with a very high purity. A purity of more than 98% can be achieved. A quantitative isolation of the compound of Formula (1) is possible by applying a solvent being capable of forming an azeotrope with the compound of Formula (1).

The present process is also suitable to perform continuous production of a compound of Formula (1) and subsequent organic synthesis.

The invention further pertains to an azeotrope of the compound of Formula (1) and a solvent capable of forming an azeotrope with the compound of Formula (1). Preferably, the azeotrope comprises the compound of Formula (1) and triethylene glycol.

The present invention is illustrated by, but not intended to be limited to, the following examples.

EXAMPLES 1-10: PREPARATION OF 1-CYCLOPROPYL-NAPHTHALENE FROM 3-DIMETHYLAMINO-1-(NAPHTHALEN-1-YL)PROPAN-1-ONE HYDROCHLORIDE

General Procedure:
3-dimethylamino-1-(naphthalen-1-yl)propan-1-one hydrochloride (50 g, E1 equivalents) and triethylene glycol (100 ml) were charged to the reactor at room temperature. 50% NaOH (E2 equivalents) was added while keeping the internal temperature at room temperature. 64% hydrazine solution in water (E3 equivalents) was added dropwise followed by heating the reaction mixture to a temperature of 80±5° C. for a period of 5 hours. Thereafter, water was distilled off in a vacuum of 30-40 mbar at a temperature of 80±5° C. The precipitated salt was separated from the reaction mixture by filtration at a temperature of approximately 80° C. and subsequently washed with triethylene glycol brought to a temperature of approximately 80° C. (20 Vol % of the total amount of triethylene glycol).

Bringing the reaction mixture to a temperature of 200±10° C. for a period of about 5 hours gave crude 1-cyclopropyl-napthalene which was isolated by azeotropic distillation at a temperature of 190±10° C. in a vacuum of 30-40 mbar. For further purification and isolation of the obtained product water was added to the distillate and the product extracted with methyl tert.-butyl ether. The organic phase was washed with water and distilled in a vacuum of 50-100 mbar at a temperature of 80° C.

The isolated pure 1-cyclopropyl-naphtalene was obtained as clear, colorless or pale yellow liquid with a boiling point of 152° C. at 13 Torr.

TABLE 1

%-Yield and purity of 1-cyclopropyl-napthalene by variation of input parameters (equivalents E1-E3) applying standard work up procedure

| Example Nr. | E1 | E2 | E3 | 1-cyclopropyl-napthalene purity (HPLC a %) | %-yield | 1-Methylnapthalene (side product) content (HPLC a %) |
|---|---|---|---|---|---|---|
| 1 | 1.0 | 1.0 | 1.0 | 98.1 | 80 | <0.05 |
| 2 | 1.0 | 1.0 | 1.1 | 97.6 | 79 | <0.05 |
| 3 | 1.0 | 0.9 | 1.0 | 96.5 | 68 | 0.16 |
| 4 | 1.0 | 1.1 | 1.0 | 97.8 | 70 | 0.35 |
| 5 | 1.0 | 0.9 | 1.1 | 92.6 | 78 | 2.81 |
| 6 | 1.0 | 1.1 | 0.9 | 98.3 | 65 | <0.05 |
| 7 | 1.0 | 1.0 | 0.95 | 98.0 | 82 | <0.05 |
| 8 | 1.0 | 1.0 | 1.05 | 98.1 | 91 | <0.05 |
| 9 | 1.0 | 1.05 | 1.05 | 97.7 | 83 | 0.42 |
| 10 | 1.0 | 0.95 | 0.95 | 96.1 | 60 | <0.05 |

All examples according to the invention result in a high yield (greater or equal to 60%) in combination with a high purity (>90%).

COMPARATIVE EXAMPLE A: PREPARATION OF 1-CYCLOPROPYL-NAPHTHALENE FROM 3-DIMETHYLAMINO-1-(NAPHTHALEN-1-YL)PROPAN-1-ONE HYDROCHLORIDE BY OMITTING THE ADDITION OF BASE AND RAISING THE AMOUNT OF ADDED HYDRAZINE 3-dimethylamino-1-(naphthalen-1-yl)propan-1-one hydrochloride (50 g, 1.00 equiv.) and triethylene glycol (100 ml) were charged to the reactor at room temperature. 64% hydrazine solution in water (19 g, 2.00 equiv.) was added dropwise while keeping the internal temperature at room temperature. Subsequently the reaction mixture was heated to a temperature of 80-85° C. for a period of 5 hours. Thereafter, water was distilled off in a vacuum of 30-40 mbar at a temperature of 80-85° C. The precipitated salt was separated from the reaction mixture by filtration at room temperature and subsequently washed with triethylene glycol at room temperature (20 vol % of the total amount of triethylene glycol).

Bringing the reaction mixture to a temperature of 200-210° C. for a period of 5 hours gave crude 1-cyclopropyl-napthalene which was isolated by azeotropic distillation at a temperature of 180-200° C. in a vacuum of 30-40 mbar. For further purification and isolation of the obtained product water was added to the distillate and the product extracted with methyl tert-butyl ether. The organic phase was washed with water and distilled in a vacuum of 6 mbar at a temperature of 50° C.

The isolated pure 1-cyclopropyl-naphtalene was obtained as clear pale yellow liquid.

| Example Nr. | 1-cyclopropyl-napthalene | | | purity (HPLC a %) | %-yield | 1-Methylnapthalene (side product) content (HPLC a %) |
| --- | --- | --- | --- | --- | --- | --- |
| | E1 | E2 | E3 | | | |
| Comp. Example A | 1.0 | 0 | 2.0 | 85.7 | 80 | 4.24 |

The invention claimed is:

1. A process for preparing a compound of Formula (1)

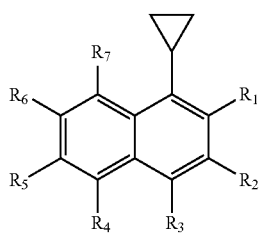

(1)

comprising the steps of a) contacting a compound of Formula (2)

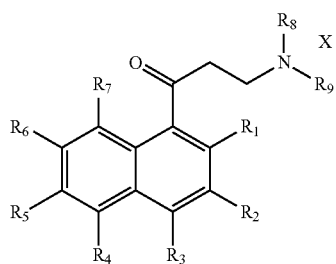

(2)

with a base and a first solvent to obtain a solution wherein a molar ratio of base to compound of Formula (2) is at least 0.7 and at most 1.3, wherein the first solvent is selected from the group consisting of triethylene glycol, sulfolane, propylene carbonate, ethylene glycol, diethylene glycol, methyl tert-butyl ether, dimethylformamide, dimethylacetamide and quinoline;

b) addition of hydrazine to the solution to obtain a compound of Formula (3)

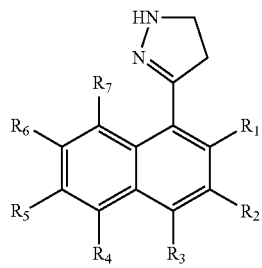

(3)

c) adding a second solvent that is different from the first solvent to the solution and/or at least partially removing the first solvent from the solution thereby obtaining a reaction mixture; and d) heating the reaction mixture to a temperature above 190° C. in the absence of a catalyst to obtain the compound of Formula (1), wherein the steps b) and c) are optionally performed concurrently; and wherein $R_1$-$R_7$ are independently hydrogen or $C_{1-8}$ alkyl, $C_{1-6}$ alkoxy, $C_{3-6}$ cycloalkyl or $C_{5-10}$ aryl, $R_8$ and $R_9$ are independently hydrogen or $C_{1-8}$ alkyl; and X is a counter ion.

2. The process according to claim 1, wherein a molar ratio of base to compound of Formula (2) in the step a) is from 0.95-1.1.

3. The process according to claim 1, wherein water is removed from the solution obtained in the step a).

4. The process according to claim 1, wherein $R_1$-$R_7$ are hydrogen.

5. The process according to claim 1, wherein $R_8$ and $R_9$ are methyl.

6. The process according to claim 1, wherein a molar ratio of hydrazine to compound of Formula (2) in the step b) is between 0.90-1.05.

7. The process according to claim 1, wherein triethylene glycol as the first or the second solvent is capable of forming an azeotrope with the compound of Formula (1).

8. The process according to claim 1, wherein the steps b) and c) are performed concurrently.

9. The process according to claim 1, wherein the second solvent is a polar solvent.

* * * * *